(12) United States Patent
Nichols et al.

(10) Patent No.: US 8,282,084 B2
(45) Date of Patent: Oct. 9, 2012

(54) RESPIRATORY HUMIDIFICATION SYSTEM

(75) Inventors: Walter A. Nichols, Chesterfield, VA (US); Christopher S. Tucker, Midlothian, VA (US); Amit Limaye, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

(21) Appl. No.: 13/240,374

(22) Filed: Sep. 22, 2011

(65) Prior Publication Data

US 2012/0006324 A1    Jan. 12, 2012

Related U.S. Application Data

(62) Division of application No. 12/285,913, filed on Oct. 16, 2008, now Pat. No. 8,052,127.

(60) Provisional application No. 60/960,908, filed on Oct. 19, 2007.

(51) Int. Cl.
*B01F 3/04* (2006.01)

(52) U.S. Cl. ........... 261/5; 261/36.1; 261/127; 261/133; 261/151; 239/127; 128/203.26

(58) Field of Classification Search .................. 261/4, 5, 261/36.1, 37, 66, 104, 127, 128, 133, 142, 261/151, 154, DIG. 65; 239/13, 127, 133, 239/136; 128/203.26, 203.27
See application file for complete search history.

(56) References Cited

U.S. PATENT DOCUMENTS

| | | | |
|---|---|---|---|
| 4,048,993 A | 9/1977 | Dobritz | |
| 4,121,583 A | 10/1978 | Chen | |
| 4,172,105 A | 10/1979 | Miller et al. | |
| 4,532,088 A | 7/1985 | Miller | |
| 5,407,604 A * | 4/1995 | Luffman | 261/4 |
| 5,713,971 A | 2/1998 | Rohrbach et al. | |
| 5,829,428 A | 11/1998 | Walters et al. | |
| 6,095,505 A | 8/2000 | Miller | |
| 6,102,037 A | 8/2000 | Koch | |
| 6,349,722 B1 | 2/2002 | Gradon et al. | |
| 6,491,233 B2 | 12/2002 | Nichols | |
| 6,501,052 B2 | 12/2002 | Cox et al. | |
| 6,516,796 B1 | 2/2003 | Cox et al. | |
| 6,526,976 B1 * | 3/2003 | Baran | 128/207.14 |

(Continued)

FOREIGN PATENT DOCUMENTS

WO        WO 01/81182 A2        11/2001

(Continued)

OTHER PUBLICATIONS

Partial International Search Report mailed Mar. 6, 2009 for PCT/EP2008/008860.

(Continued)

*Primary Examiner* — Charles Bushey
(74) *Attorney, Agent, or Firm* — Buchanan Ingersoll & Rooney PC

(57) ABSTRACT

A respiratory humidification system having a capillary passage in communication with a ventilator, the ventilator adapted to deliver an air stream, a heater operable to at least partially vaporize water in the capillary passage, a pumping unit adapted to supply water to the capillary passage, wherein the water upon heating is at least partially vaporized to form an aerosol stream. The aerosol stream is combined with the air stream to form a humidified air stream.

17 Claims, 11 Drawing Sheets

U.S. PATENT DOCUMENTS

| | | |
|---|---|---|
| 6,557,551 B2 | 5/2003 | Nitta |
| 6,568,390 B2 | 5/2003 | Nichols et al. |
| 6,601,776 B1 | 8/2003 | Oljaca et al. |
| 6,622,938 B2 * | 9/2003 | Fischer et al. ............... 239/124 |
| 6,640,050 B2 | 10/2003 | Nichols et al. |
| 6,701,921 B2 | 3/2004 | Sprinkel, Jr. et al. |
| 6,715,487 B2 | 4/2004 | Nichols et al. |
| 6,772,757 B2 * | 8/2004 | Sprinkel, Jr. ............. 128/203.26 |
| 6,799,572 B2 | 10/2004 | Nichols et al. |
| 6,804,458 B2 | 10/2004 | Sherwood et al. |
| 6,923,179 B2 * | 8/2005 | Gupta et al. ............. 128/203.17 |
| 7,066,452 B2 * | 6/2006 | Rotering et al. ............. 261/142 |
| 7,077,130 B2 | 7/2006 | Nichols et al. |
| 7,159,507 B2 | 1/2007 | Grollimund et al. |
| 7,225,998 B2 * | 6/2007 | Pellizzari ...................... 239/136 |
| 7,500,479 B2 * | 3/2009 | Nichols et al. ........... 128/200.23 |
| 7,518,123 B2 * | 4/2009 | Howell et al. ................. 250/425 |
| 7,525,663 B2 | 4/2009 | Kwok et al. |
| 7,712,729 B2 | 5/2010 | Kabasawa et al. |
| 7,730,568 B2 * | 6/2010 | Wong et al. ...................... 8/148 |
| 7,938,113 B2 | 5/2011 | Weinstein et al. |
| 7,975,687 B2 | 7/2011 | Gründler et al. |
| 8,052,127 B2 * | 11/2011 | Nichols et al. ................ 261/128 |
| 2006/0012057 A1 | 1/2006 | Anthony |
| 2008/0110458 A1 * | 5/2008 | Srinivasan et al. ....... 128/203.26 |
| 2009/0310950 A1 * | 12/2009 | Maharajh et al. ............. 392/397 |

FOREIGN PATENT DOCUMENTS

| | | |
|---|---|---|
| WO | WO 03/099367 A2 | 12/2003 |

OTHER PUBLICATIONS

International Search Report and Written Opinion mailed May 19, 2009 for PCT/EP2008/008860.

International Preliminary Report on Patentability issued Apr. 29, 2010 for PCT/EP2008/008860.

* cited by examiner

FIG. 9

Capillary Type: K32EG inner diameter = 0.0073", length 1.3"

| Power (Watts) | Flow Rate (uL/sec) | | | | | |
|---|---|---|---|---|---|---|
| | 5 | 10 | 15 | 20 | 25 | 30 |
| 5 | 4.35 | 1.45 | 0 | 1.45 | 1.45 | 2.9 |
| 7 | 7.25 | 5.8 | 0 | 1.45 | 1.45 | 2.9 |
| 9 | 10.15 | 10.15 | 5.8 | 1.45 | 1.45 | 2.9 |
| 10 | 13.05 | 11.6 | 10.15 | 1.45 | 2.9 | 2.9 |
| 12 | 17.4 | 15.95 | 14.5 | 10.15 | 7.25 | 4.35 |
| 14 | 23.2 | 20.3 | 18.85 | 14.5 | 10.15 | 8.7 |
| 15 | 30.45 | 26.1 | 24.65 | 20.3 | 17.4 | 13.05 |
| 18 | | 29 | 29 | 24.65 | 21.75 | 18.85 |
| 20 | | 34.8 | 33.35 | 30.45 | 27.55 | 24.65 |
| 22 | | 37.7 | 39.15 | 34.8 | 31.9 | 30.45 |
| 24 | | 43.5 | 43.5 | 40.6 | 34.8 | 33.35 |
| 26 | | 49.3 | 46.4 | 46.4 | 42.05 | 39.15 |
| 28 | | 56.55 | 52.2 | 50.75 | 46.4 | 43.5 |
| 30 | | | 59.45 | 55.1 | 52.2 | 49.3 |
| 32 | | | 63.8 | 59.45 | 58 | 55.1 |
| 34 | | | 69.6 | 68.15 | 63.8 | 60.9 |
| 36 | | | 75.4 | 71.05 | 68.15 | 66.7 |
| 38 | | | 81.2 | 78.3 | 73.95 | 73.95 |
| 40 | | | | 85.55 | 76.85 | 79.75 |
| 42 | | | | 88.45 | 89.9 | 84.1 |
| 44 | | | | 95.7 | 94.25 | 91.35 |
| 46 | | | | 100.05 | 100.05 | 97.15 |
| 48 | | | | 105.85 | 102.95 | 104.4 |
| 50 | | | | 111.65 | 108.75 | 111.65 |
| 52 | | | | | 116 | 118.9 |
| 54 | | | | | 121.8 | 123.25 |
| 56 | | | | | 124.7 | 129.05 |
| 58 | | | | | 131.95 | 133.4 |
| 60 | | | | | 137.75 | 140.65 |
| 62 | | | | | | 145 |
| 64 | | | | | | 150.8 |
| 66 | | | | | | 153.7 |

| Aerosol quality key | | | |
|---|---|---|---|
| Wet | | Good | |
| OK | | NA | |
| values in cells = p

FIG. 10

Capillary Type: 32G inner diameter = 0.0048", length 1.3"

| Power (Watts) | Flow Rate (uL/sec) | | | | | |
|---|---|---|---|---|---|---|
| | 5 | 10 | 15 | 20 | 25 | 30 |
| 5 | 18.85 | 8.7 | 7.25 | 10.15 | 13.05 | 14.5 |
| 7 | 30.45 | 21.75 | 7.25 | 10.15 | 13.05 | 14.5 |
| 9 | 43.5 | 40.6 | 7.25 | 10.15 | 13.05 | 14.5 |
| 10 | 47.85 | 46.4 | 7.25 | 10.15 | 13.05 | 14.5 |
| 12 | 59.45 | 59.45 | 47.85 | 10.15 | 13.05 | 14.5 |
| 14 | 76.85 | 75.4 | 68.15 | 39.15 | 13.05 | 14.5 |
| 15 | 88.45 | 87 | 78.3 | 53.65 | 42.05 | 39.15 |
| 18 | | 101.5 | 95.7 | 69.6 | 68.15 | 47.85 |
| 20 | | 116 | 111.7 | 79.75 | 84.1 | 68.15 |
| 22 | | 130.5 | 127.6 | 94.25 | 98.6 | 56.55 |
| 24 | | 142.1 | 142.1 | 111.65 | 114.55 | 105.85 |
| 26 | | 162.4 | 156.6 | 130.5 | 129.05 | 113.1 |
| 28 | | 174 | 175.5 | 150.8 | 149.35 | 130.5 |
| 30 | | | 181.3 | 165.3 | 166.75 | 150.8 |
| 32 | | | 190 | 181.25 | 184.15 | 166.75 |
| 34 | | | 203 | 198.65 | 205.9 | 185.6 |
| 36 | | | 217.5 | 214.6 | 223.3 | 201.55 |
| 38 | | | 250.9 | 230.55 | 236.35 | 220.4 |
| 40 | | | 262.5 | 246.5 | 258.1 | 242.15 |
| 42 | | | 274.1 | 261 | 276.95 | 259.55 |
| 44 | | | | 276.95 | 287.1 | 275.5 |
| 46 | | | | 294.35 | 305.95 | 294.35 |
| 48 | | | | 308.85 | 320.45 | 308.85 |
| 50 | | | | 320.45 | 332.05 | 324.8 |
| 52 | | | | 337.85 | 346.55 | 340.75 |
| 54 | | | | 348 | 358.15 | 361.05 |
| 56 | | | | | 374.1 | 372.65 |
| 58 | | | | | 385.7 | 388.6 |
| 60 | | | | | 398.75 | 401.65 |
| 62 | | | | | 416.15 | 417.6 |
| 64 | | | | | 429.2 | 433.55 |
| 66 | | | | | | 449.5 |
| 68 | | | | | | 459.65 |
| 70 | | | | | | 475.6 |

| Aerosol quality key | | | |
|---|---|---|---|
| Wet | | Good | |
| OK | | NA | |
| values in cells = pressure - psig | | | |

FIG. 11

Capillary Type: 32G inner diameter = 0.0048", length 1.3", orifice 0.00314"

| Power (Watts) | Flow Rate (uL/sec) | | | | | |
|---|---|---|---|---|---|---|
| | 5 | 10 | 15 | 20 | 25 | 30 |
| 5 | 14.5 | 8.7 | 4.35 | 4.35 | 4.35 | 8.7 |
| 7 | 31.9 | 18.85 | 4.35 | 4.35 | 4.35 | 8.7 |
| 9 | 47.85 | 31.9 | 18.85 | 4.35 | 4.35 | 8.7 |
| 10 | 56.55 | 37.7 | 24.65 | 14.5 | 4.35 | 8.7 |
| 12 | 76.85 | 55.1 | 39.15 | 27.55 | 4.35 | 8.7 |
| 14 | | 68.15 | 53.65 | 37.7 | 29 | 8.7 |
| 15 | | 87 | 68.15 | 50.75 | 33.35 | 29 |
| 18 | | 107.3 | 82.65 | 65.25 | 50.75 | 40.6 |
| 20 | | 121.8 | 101.5 | 81.2 | 62.35 | 52.2 |
| 22 | | 139.2 | 117.45 | 95.7 | 76.85 | 65.25 |
| 24 | | 156.6 | 136.3 | 113.1 | 94.25 | 75.4 |
| 26 | | | 153.7 | 130.5 | 111.65 | 94.25 |
| 28 | | | 174 | 149.35 | 130.5 | 107.3 |
| 30 | | | 191.4 | 166.75 | 147.9 | 126.15 |
| 32 | | | 210.25 | 185.6 | 166.75 | 143.55 |
| 34 | | | 230.55 | 208.8 | 185.6 | 160.95 |
| 36 | | | | 221.85 | 204.45 | 181.25 |
| 38 | | | | 240.7 | 220.4 | 198.65 |
| 40 | | | | 259.55 | 239.25 | 213.15 |
| 42 | | | | 281.3 | 259.55 | 232 |
| 44 | | | | 298.7 | 275.5 | 250.85 |
| 46 | | | | 314.65 | 291.45 | 269.7 |
| 48 | | | | | 319 | 288.55 |
| 50 | | | | | 323.35 | 305.95 |
| 52 | | | | | 343.65 | 321.9 |
| 54 | | | | | 361.05 | 4689.3 |
| 56 | | | | | 378.45 | 356.7 |
| 58 | | | | | 394.4 | 377 |
| 60 | | | | | 413.25 | 391.5 |
| 62 | | | | | 429.2 | 411.8 |
| 64 | | | | | | 423.4 |
| 66 | | | | | | 450.95 |
| 68 | | | | | | 464 |
| 70 | | | | | | 481.4 |

| Aerosol quality key | | | |
|---|---|---|---|
| Wet | | Good | |
| OK | | NA | |
| values in cells = pressure - psig | | | |

FIG. 12

| Capillary Type: K32EG inner diameter = 0.0073", length 1.3" | | | | |
|---|---|---|---|---|
| | Flow Rate (uL/sec) | | | |
| Power (Watts) | 5 | 10 | 15 | 20 |
| 5 | 39.7 | 47 | | |
| 7 | 38.8 | 52 | | |
| 9 | 41.1 | 57 | 64 | |
| 10 | 42.7 | 57.3 | 65.5 | |
| 12 | 47.5 | 61.6 | 71.4 | 75.1 |
| 14 | 49.9 | 65.2 | 73.3 | 79.7 |
| 15 | 51 | 69.6 | 77.3 | 83.9 |
| 18 | | 69.8 | 81 | 84.9 |
| 20 | | 72.4 | 84.6 | 89.9 |
| 22 | | 76 | 88.1 | 93 |
| 24 | | 77.1 | 93.4 | 94.9 |
| 26 | | 77.9 | 97.3 | 98 |
| 28 | | | 98.9 | 99.6 |
| 30 | | | 100 | 100 |
| 32 | | | 100 | 100 |
| 34 | | | 100 | 100 |
| 36 | | | 100 | 100 |
| 38 | | | 100 | 100 |
| 40 | | | 100 | 100 |
| Inlet air RH% | 15.5 | 18.1 | 17.6 | 18.3 |

| Aerosol quality key | | | |
|---|---|---|---|
| Wet | | Good | |
| OK | | NA | |
| values in cells = RH% | | | |

| PARTICLE SIZE EXIT CAPILLARY 26G x 33 mm | | | | |
|---|---|---|---|---|
| Flow Rate = 1.2g/min | | | | |
| Power (Watts) | D90 pm | D50 pm | G SD | RH |
| 17 | 16.81 | 6.37 | 2.64 | 75% |
| 20 | 12.78 | 4.93 | 2.59 | 80% |
| 23 | 10.02 | 5.43 | 1.85 | 85% |
| 26 | 6.37 | 3.55 | 1.79 | 90% |
| 30 | 9.04 | 1.12 | 8.07 | 100% |
| 32 | 7.17 | 1.14 | 6.29 | 100% |
| 34 | 6.86 | 1.14 | 6.02 | 100% |
| 36 | 5.41 | 1.10 | 4.92 | 100% |
| 38 | 4.56 | 1.06 | 4.30 | 100% |
| 40 | 3.70 | 1.04 | 3.56 | 100% |
| 42 | 3.70 | 1.04 | 3.56 | 100% |

Note - D50 and D90 represent the median or the 50th percentile and the 90th percentile of the particle size distribution, respectively, as measured by volume, i.e., the D50 (D90) is a value on the distribution such that 50% (90%) of the particles have a volume of this value or less

FIG. 13

RESPIRATORY HUMIDIFICATION SYSTEM

CROSS-REFERENCE TO RELATED APPLICATION

This application is a divisional of U.S. patent application Ser. No. 12/285,913, entitled RESPIRATORY HUMIDIFICATION SYSTEM, filed on Oct. 16, 2008, now U.S. Pat. No. 8,052,127, issued Nov. 8, 2011, which claims priority to U.S. Patent Provisional Application No. 60/960,908, filed Oct. 19, 2007, the entire content of each is incorporated herein by reference in its entirety.

SUMMARY

In accordance with one embodiment, a respiratory humidification system, comprises: a capillary passage in communication with a ventilator, the ventilator adapted to deliver an air stream; a heater operable to at least partially vaporize water in the capillary passage; a pumping unit adapted to supply water to the capillary passage, wherein the water upon heating is at least partially vaporized to form an aerosol stream, and wherein the aerosol stream is combined with the air stream to form a humidified air stream; a controller having an on-off switch and programmed such that the controller is configured to continuously operate the pump and to maintain the capillary in a heated condition when the controller switch is on; and a water recirculation arrangement to accommodate continuous operation of the pumping unit.

In accordance with another embodiment, a respiratory humidification system, comprises: a heated capillary passage adapted to receive water from a pressurized water supply, which is at least partially vaporized within the heated capillary passage to form an aerosol stream, the heated capillary passage comprising: a capillary passage adapted to form an aerosol when the pressurized water in the capillary passage is heated to volatilize at least some of the pressurized water therein; and a heater arranged to heat the pressurized water in the capillary passage into at least a partially vaporized state; a pumping unit adapted to supply the pressurized water to the capillary passage; a filter operable to demineralize the pressurized water; and a ventilator adapted to deliver an air stream, and wherein the aerosol stream is combined with the air stream to form a humidified gas stream.

In accordance with a further embodiment, a respiratory humidification system having an enhanced capacity to operate with mineral laden water, the system comprises: a coated capillary passage whose operating temperature is in the range of 120 to 130 degrees Celsius, and which is in communication with a ventilator, the ventilator adapted to deliver an air stream; a heater operable to at least partially vaporize water in the capillary passage; and a pumping unit adapted to supply water to the capillary passage, wherein the water upon heating is at least partially vaporized to form an aerosol stream, and wherein the aerosol stream is combined with the air stream to form a humidified air stream.

In accordance with another embodiment, a method of delivering a humidified air stream comprises: supplying water to a capillary passage, wherein the water is supplied to the capillary passage at a pressure of 10 to 80 psig (pound-force per square inch gauge) and at a constant flow rate of 0.25 cc/minute to 2.2 cc/minute (cubic centimeters per minute); vaporizing at least a portion of the water within the capillary passage to form an aerosol stream; supplying an air stream from a ventilator; combining the aerosol stream and the air stream to form a humidified gas stream; and discharging the humidified air stream.

BRIEF DESCRIPTION OF THE DRAWINGS

FIG. 9 is a table showing the results of flow rate ($\mu$l/sec) versus power (watts) for a heated capillary tube having an inner diameter of 0.0073 inches and a length of 1.3 inches and the resultant aerosol quality.

FIG. 10 is a table showing the results of flow rate ($\mu$l/sec) versus power (watts) for a heated capillary tube having an inner diameter of 0.0048 inches and a length of 1.3 inches and the resultant aerosol quality.

FIG. 11 is a table showing the results of flow rate ($\mu$l/sec) versus power (watts) for a heated capillary tube having an inner diameter of 0.0048 inches, an orifice on a downstream end of the capillary of 0.00314 inches and a length of 1.3 inches and the resultant aerosol quality.

FIG. 12 is a table showing the results of flow rate ($\mu$l/sec) versus power (watts) for a heated capillary tube having an inner diameter of 0.0073 inches and a length of 1.3 inches and the resultant aerosol quality (relative humidity).

FIG. 13 is a table showing the particle size of an aerosol within the aerosol stream exiting a capillary passage.

DETAILED DESCRIPTION

Typical humidification systems for home-use or hospital-use with CPAP (continuous positive airway pressure) ventilation commonly experience condensation within the respiratory tubing. As a result, the humidification system requires a means for redirecting the condensation away from the patient and draining it out of the respiratory tubing. Moreover, the losses associated with such condensation require more frequent filling of the water reservoir.

In addition, typical passover humidification systems rely on humidifying the air or gas stream by contacting it with a large surface area or volume of heated water. However, the dynamic response times of such passover humidification systems are typically slow. In particular they are slow to change the relative humidity (RH) with shifts in the flow rate.

Accordingly, it would be desirable to have a humidification system, which is able to overcome these deficiencies by using a heated capillary passage to provide up to 100% relative humidity (RH) to a ventilation air stream having a high flow rate (e.g., a flow rate of up to 50 liters/min). In addition, it would be desirable to control the relative humidity from ambient RH to 100% RH based on the flow rate of water supplied through the capillary passage.

Figure 1:
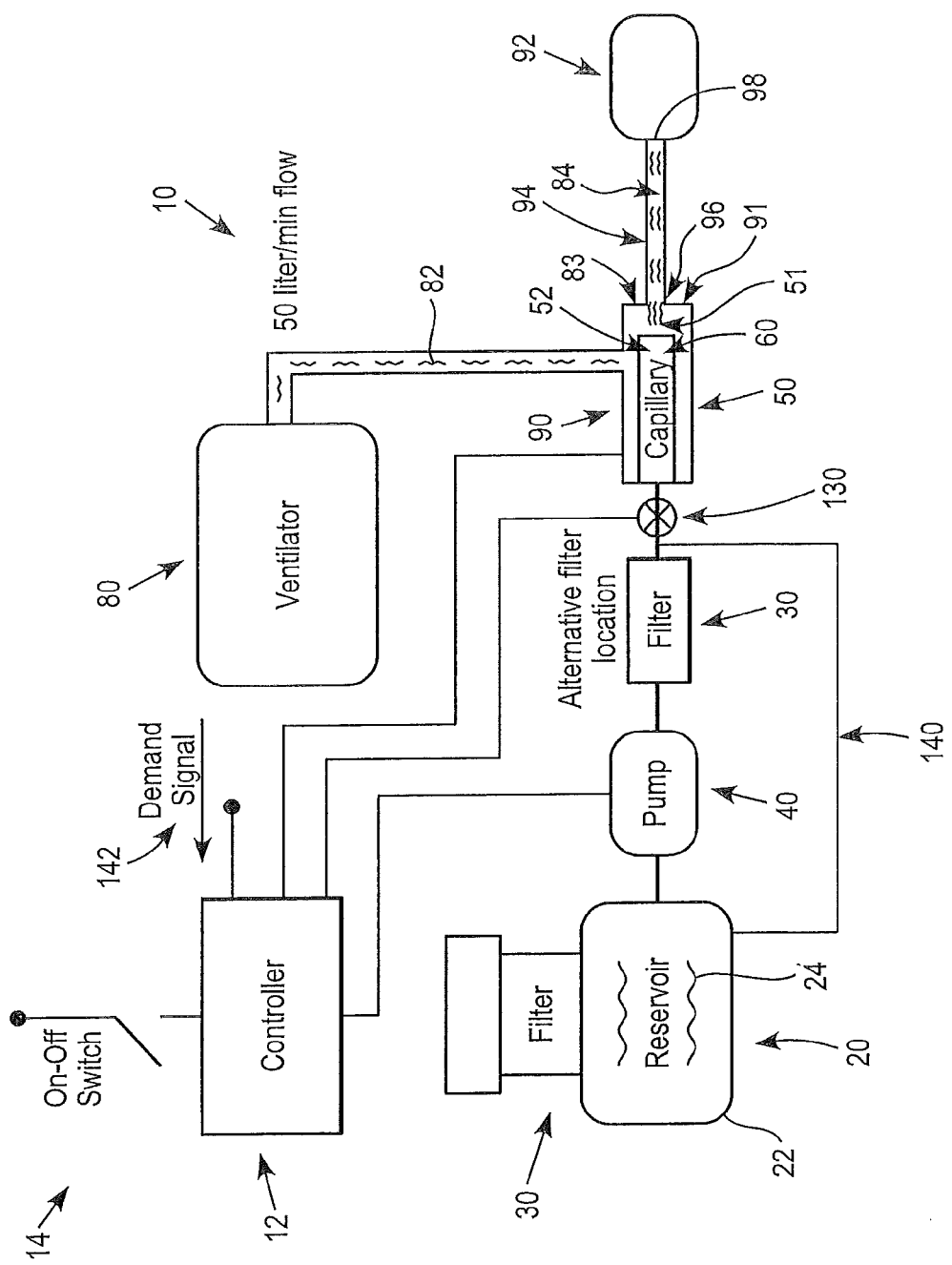
FIG. 1 is a diagram of a respiratory humidification system in accordance with one embodiment.

The humidification system 10 illustrated in FIG. 1 overcomes aforementioned deficiencies of the prior art. As shown in FIG. 1, the respiratory humidification system 10 includes a controller 12 having an on/off switch 14, a liquid supply 20, a filter assembly (or filter) 30, a pumping unit 40, a capillary unit 50 having a heated capillary passage 52 (i.e., capillary), and a ventilator 80 adapted to deliver an air stream 82.

The liquid supply 20 includes a reservoir 22 containing a suitable fluid or liquid material (e.g., water) 24 in liquid phase, which is capable of being volatilized within the heated capillary passage 52. In one preferred embodiment, the liquid supply 20 delivers water ($H_2O$); however, other suitable liquid materials can be used. The water 24 is supplied to the capillary unit 50 via the pumping unit 40. The pumping unit 40 preferably delivers the water 24 to the capillary unit 50 at a constant flow rate ranging from about 0.25 cc/min to about 2.2 cc/min. If desired, the water 24 can be stored within the reservoir 22 at a pressure above atmospheric to facilitate delivery of the water 24 to the fluid or capillary passage 52.

In one embodiment, the water 24 is contained within a refillable storage chamber or reservoir 22 formed of a material suitable for containing the water 24 to be volatilized. Alternatively, the water 24 is contained within a disposable storage chamber or reservoir 22 (such as a bag of sterilized and/or distilled water), which, upon exhaustion of water 24, is discarded and replaced by a new storage chamber or reservoir 22.

As shown in FIG. 1, the system 10 also includes a filter assembly 30, which is adapted to remove minerals from the water 24. It can be appreciated that the presence of mineral deposits in water supplies, including pressurized water lines can inhibit heat transfer within the capillary passage 52, which can lead to poor performance of the system 10. In addition, typical tap water will often leave mineral deposits within the capillary passage 52, (e.g., a capillary tube 60 within the capillary unit 50), which can lead to an occlusion of the capillary passage 52.

The filter assembly 30 can be located either upstream or downstream of the pumping unit 40 depending on the pressure drop introduced by the filter assembly 30. In a preferred embodiment, the filter or filter assembly 30 is placed on the upstream side of the pumping unit 40, such that the water 24 is filtered before the pumping unit 40 pumps the water 24 to the capillary unit 50. In one embodiment, the filter assembly or filter 30 is an ion-exchange resin filter, which removes the mineral deposits from the water 24.

The pumping unit 40 receives the water 24 from the reservoir 22 and pumps the water 24 to the heated capillary passage 52 (or fluid passage) within the capillary unit 50, wherein the water 24 is at least partially vaporized into an aerosol stream 83. The pumping unit 40 can be any suitable pumping device, which can supply adequate pressure and positive metering to the capillary unit 50, such as a peristaltic pump, a gear pump, or a piston pump. In accordance with one embodiment, a peristaltic pump is preferred since the wetted path is comprised of replaceable tubing.

In accordance with one embodiment, the pumping unit 40 delivers pressurized water 24 at approximately 10 to 80 psig (pound-force per square inch gauge) at a constant flow rate ranging from about 0.25 cc/min to 2.2 cc/min (cubic centimeter per minute) to the heated capillary passage 52. The ventilator 80 preferably delivers an air stream 82, which is combined with the aerosol stream 83 from the capillary passage 52 to form a humidified air stream 84. The humidified air stream (or humidified gas stream) 84 is then discharged through a patient interface device 92.

In accordance with an embodiment, the capillary unit 50 within the system 10 generates an aerosol stream 83 of water droplets having a particle size of less than 10 microns and more preferably with a particle size of approximately 1 to 2 microns, which is entrained with the air stream 82 (e.g., up to 50 liters/minute) of the ventilator 80. The water droplets within the aerosol stream 83 evaporate within the air stream 82 so as to establish a humidified air stream 84. In accordance with one embodiment, the aerosol stream 83 from the capillary passage 52 is directed in a coaxial relation with respect to the air stream 82 from the ventilator 80.

It can be appreciated that a system 10 as shown in FIG. 1 has a high air flow rate (e.g., up to 50 liters per minute), which capacity assists in the evaporation of aerosol particles 51 produced by the capillary unit 50. Consequently, a humidification system 10 has very little condensation over long operating times. In addition, the low condensation rate also provides the system 10 with design flexibility in regards to the placement of the capillary unit 50 within the system. For example, if desired the capillary unit 50 can be in close proximity to a patient or alternatively incorporated in the main body of a base unit 200 (FIGS. 6-8) containing the pumping unit 40 and support electronics, including the control circuit 240 (FIG. 7).

Figure 4A:
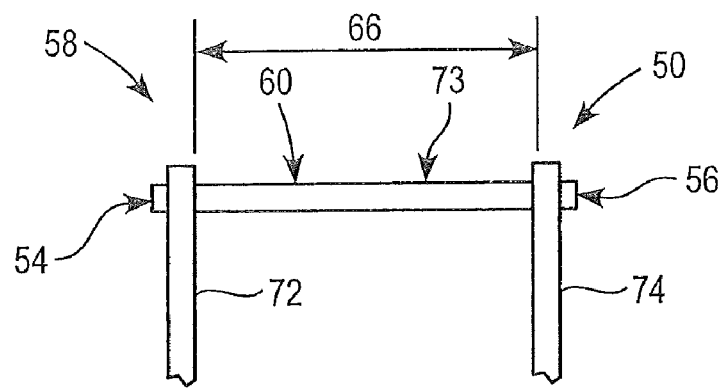
FIG. 4A is a side view of a heated capillary tube and a heating element in accordance with one embodiment.
Figure 4B:
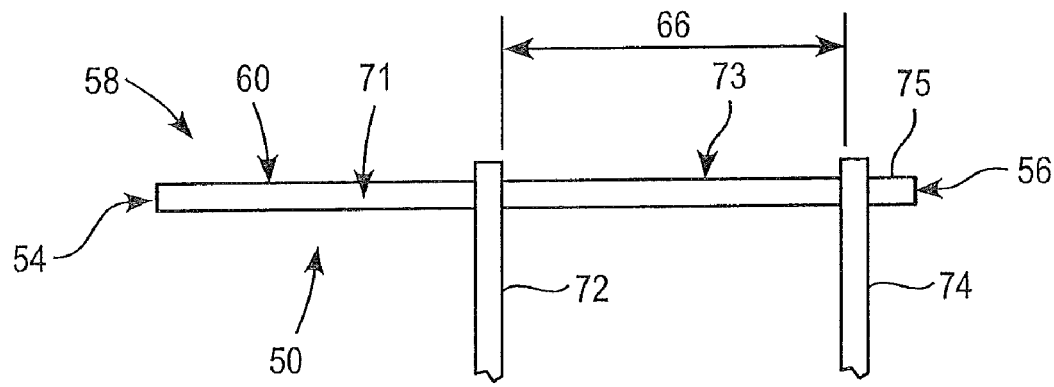
FIG. 4B is a side view of a heated capillary tube and a heating element in accordance with another embodiment.

The capillary unit 50 includes a heated fluidic path or capillary passage 52 capable of at least partially vaporizing the water 24. In accordance with one embodiment, the capillary unit 50 includes a capillary tube 60 having an inlet end 54, an outlet end 56, and a heating system 58 (FIGS. 4A and 4B). The heating system 58 can be a pair of electrodes (or contacts) 72, 74 comprised of at least one upstream electrode 72 and one downstream electrode 74 connected to the capillary tube 60 by known means such as brazing or welding.

In accordance with one embodiment, the water 24 flows through the capillary tube 60 into a heated section 73 (FIGS. 4A and 4B) between the pair of electrodes 72, 74, wherein the fluid is heated and converted to a vapor or aerosol stream 83. The aerosol stream 83 passes from the heated section 73 of the capillary tube 60 to the end of the capillary tube 60 and exits from the outlet end 56 of the capillary tube 60. The volatilized fluid in the form of an aerosol stream 83 exits from the capillary tube 60 and is combined with the air stream 82 from the ventilator 80 forming a humidified air stream 84, which is discharged for purposes such as maintaining humidity levels in a closed space or delivery to a patient, animal or plant.

The capillary unit 50 can be contained within a housing 90 that interfaces with the air stream 82 from the ventilator 80. In accordance with one embodiment, the air stream 82 is preferably delivered at approximately 10 to 70 liters-per-minute (LPM), and more preferably about 5 to 50 liters-per-minute (LPM). To control the delivery of the breathing gas or air stream 82 to the patient, the ventilator 80 can include at least one selectable ventilator setting control operatively connected to a processing system for governing the supply of ventilation support or air stream 82 to the patient.

The system 10 also preferably includes a CPAP adaptor or other suitable patient interface device 92 for purposes such as maintaining humidity levels in a closed space or delivery to a patient, animal or plant. It can be appreciated that the air stream 82 may be from a hospital-compressed airline or pressurized air source, such as a tank of compressed air with a suitable valve arrangement to achieve a desired airflow. In accordance with one embodiment, the respiratory tube or flow tube 94 has an inlet 96 in communication with an outlet 91 of the housing 90. The respiratory tube or flow tube 94 also has an outlet 98, which is connected to the patient interface device 92. It can be appreciated that the respiratory tube or flow tube 94 preferably has a length of approximately 2 to 6 feet extending from the housing 90 to the CPAP adaptor, nasal prongs, mask, mouthpiece or other suitable patient interface device 92.

A programmable automation controller (not shown) preferably controls the pumping unit 40, as well as the heating of the capillary unit 50 including the capillary passage 52. The controller can be any suitable microprocessor or programmable automation controller (PAC), such as the CompactRIO® sold by National Instruments. In accordance with one embodiment, the controlling of the system 10 including the algorithm to control the power to the electrodes 72, 74 (FIGS. 4A and 4B) can be based on the monitoring of the resistance or temperature of the capillary passage 52, such as disclosed in U.S. Pat. Nos. 6,640,050 and 6,772,757, the disclosures of which are incorporated herein in their entirety.

In use, the system 10 is responsive to changes in relative humidity (RH) as a result of the low mass of the capillary unit 50 including the capillary passage 52 and the small mass of water 24 (i.e., pressurized water) being heated. In addition, the ability of the pumping unit 40 to change or adjust the flow rate of water 24 to the capillary unit 50 provides the system 10 with the ability to shift or change the relatively humidity (RH) of the humidified gas stream 84 within milliseconds. Thus, by measuring the patient's airflow, the system 10 can deliver a humidified gas stream 84 with a desired relative humidity by simply changing the liquid material's 24 (i.e., water) flow rate from the pumping unit 40. Additionally, the system 10 allows for the starting and stopping of the system 10 within milliseconds, creating a system 10 that is responsive to the breathing profile of the patient. Accordingly, in one embodiment, the flow rate of the water 24 to the capillary passage 52 can be an intermittent or pulse delivery to coincide with the breathing profile of the patient. The low condensation rate of the humidification system 10 also affords design flexibility in the placement of the capillary unit 50 within the system 10. For example, the capillary unit 50 can be placed in close proximity to the patient, or alternatively incorporated in a separate unit containing the pumping unit 40 and support electronics and components.

Referring to FIG. 1, in accordance with another embodiment, the system 10 preferably includes a valve 130 (e.g. solenoid) located upstream of the capillary unit 50, a controller 12 programmed to maintain the capillary passage 52 in a heated condition at a preferred operating temperature and a water recirculation arrangement (or recirculation passage) 140, which in cooperation with the valve 130 permits the pumping unit 40 to remain in a continuously running condition. It can be appreciated that with such arrangement, when the controller 12 receives a demand signal 142 from the control electronics 200 (FIG. 6), the system 10 immediately delivers water to the heated capillary 52, which being already heated, immediately creates and discharges an aerosol of water vapor within a minimal response time. Alternatively, when the system 10 is turned off via an on-off switch 14, the heater (not shown) to the capillary 52 and the pumping unit 40 are shut down and the valve 130 remains closed.

It can be appreciated that the system 10 can be occasionally and/or accidentally operated with tap water having a mineral content that could clog the capillary passage 52. Accordingly, in accordance with a further embodiment, a reduction of mineral deposits along an interior surface of the capillary passage 52 can be obtained by coating the interior surfaces of the capillary passage 52 with a fluorine-containing polymer such as Teflon® or a similar substance, and reducing the operating temperature of the heated capillary passage 52 to approximately 120 to 130 degrees Celsius. In addition, by reducing the operating temperature of the heated capillary passage 52, a reduced vapor region within the capillary passage 52 is formed, thereby reducing the opportunity for minerals to deposit therein. For example, in accordance with a preferred embodiment, the Teflon coating is sufficient to reduce adhesion of mineral deposits along the interior surfaces of the capillary or capillary passage 52.

In accordance with another embodiment, the discharge of the capillary passage 52 is preferably co-directional or more preferably, co-axial with respect to the direction of the flow stream of the ventilator 80 with which it is mixed, and wherein by such arrangement, losses through impaction are minimized.

Figure 2:
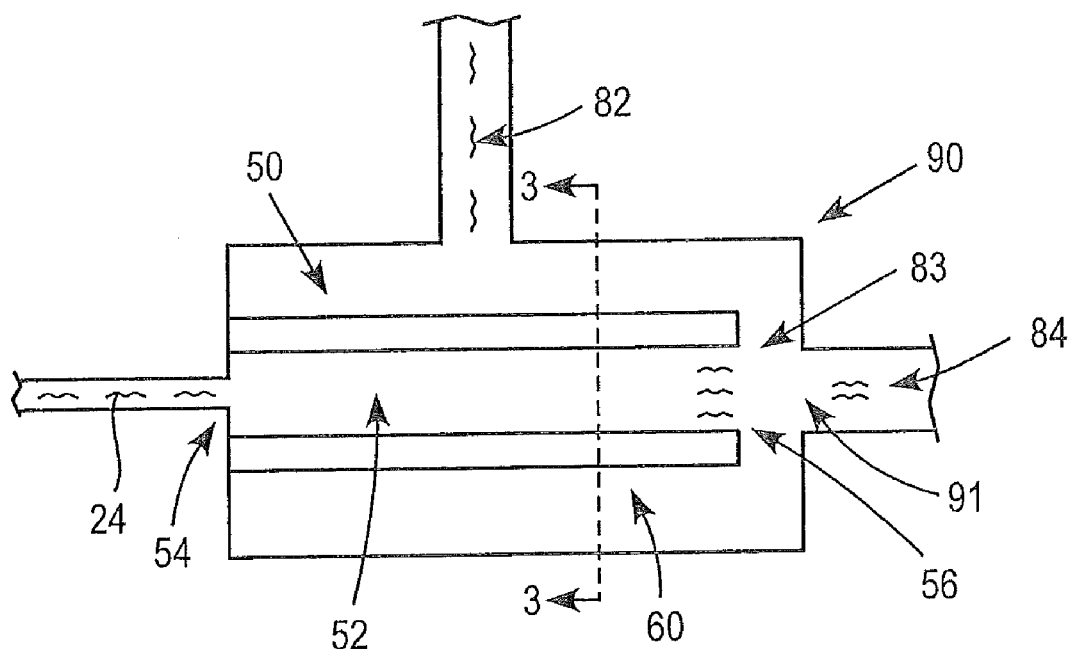
FIG. 2 is a cross-sectional view of an aerosol generator in the form of a capillary tube in accordance with one embodiment.

FIG. 2 shows a cross-sectional view of a housing 90, which includes a heated capillary unit 50 in the form of a capillary tube (or passage) 60 in accordance with one embodiment. As shown in FIG. 2, the capillary unit 50 includes a capillary tube 60 having a fluidic path or capillary passage 52 with an inlet 54 and an outlet 56 (or exit end). The inlet 54 receives the water 24 preferably in the form of pressurized water from the pumping unit 40 with an upstream filter system 30, or from the pumping unit 40 with a downstream filter system 30. The water 24 enters the inlet 54 of the capillary tube 60 in the form of a liquid or fluid. In accordance with one embodiment, the water 24 will be at least partially vaporized within the capillary passage 52 into an aerosol stream 83 and exits the capillary passage 52 at the outlet or exit end 56 of the capillary passage 52. The aerosol stream 83 from the capillary tube 60 interfaces with the air stream 82 from the ventilator 80 at the exit end 56 of the capillary passage 52 forming a humidified air stream 84.

The capillary tube 60 can be comprised of a metallic or non-metallic tube, including such materials as stainless steel, a nickel-based super alloy such as Inconel, or glass. Alternatively, the capillary assembly or tube 60 may be comprised of, for example, fused silica or aluminum silicate ceramic, or other substantially non-reactive materials capable of withstanding repeated heating cycles and generated pressures and having suitable heat conduction properties.

Figure 3:
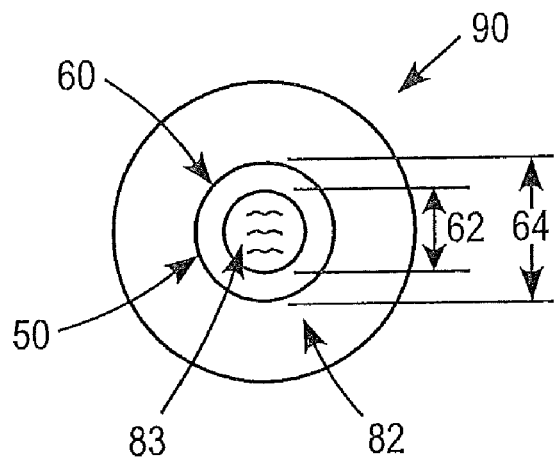
FIG. 3 is a cross-sectional view of the aerosol generator of FIG. 2 along the lines 3-3.

FIG. 3 shows a cross-sectional view of the housing 90 and the capillary unit 50 of FIG. 2 along the line 3-3. As shown in FIG. 3, the aerosol stream 83 from the capillary tube 60 is preferably coaxial or centered within the air stream 82 from the ventilator 80 as the aerosol stream 83 exits from the capillary tube 60 within the housing 90. In accordance with one embodiment, the capillary or capillary tube 60 is preferably a metallic or stainless steel tube having an inner diameter 62 of approximately 0.0020 to 0.020 inches and more preferably an inner diameter 62 of approximately 0.0080 inches to 0.020 inches, and an outer diameter 64 of approximately 0.005 to 0.032 inches, and more preferably an outer diameter 64 of approximately 0.012 inches to 0.032 inches.

FIG. 4A shows a side view of a heated capillary tube 60 and a heating system (or heater) 58 according to one embodiment. As shown in FIG. 4A, the heating system 58 includes an electrode assembly comprised of a pair of electrodes (or contacts) 72, 74, which are applied to the capillary tube 60 to provide a resistive path that connects to a controlled power supply (not shown). The electrodes 72, 74 are preferably located at the inlet end 54 of the capillary tube 60 and the exit end 56 of the capillary tube 60 forming a heated section 73 between the two electrodes 72, 74. A voltage applied between the two electrodes 72, 74 generates heat in the heated section 73 based on the resistivity of the stainless steel or other material making up the capillary tube 60 or heating elements or heater, and other parameters such as the cross-sectional area and length of the heated section 73. The power applied between the two electrodes 72, 74 can be between about 1 to 70 watts, and more preferably 5 to 50 watts.

The heated section 73 preferably has a heated length 66 of about 0.98 inches (25 mm) to 2.95 inches (75 mm), and more preferably a heated length 66 of about 0.98 inches (25 mm) to 1.38 inches (35 mm). In a preferred embodiment, the capillary tube 60 does not include a tipped capillary having a reduced diameter at the exit end 56 of the capillary tube 60.

FIG. 4B shows a side view of a heated capillary tube 60 and a heating system 58 in accordance with another embodiment. As shown in FIG. 4B, the heating system 58 includes an electrode assembly comprised of a pair of electrodes (or contacts) 72, 74, which are applied to the capillary tube 60 to provide a resistive path that connects to a controlled power supply (not shown). The electrodes 72, 74 are connected at spaced positions along the length of the capillary tube 60, with a feed (or proximal) section 71 being defined between the inlet end 54 of the capillary tube 60 and the upstream electrode 72, a heated section 73 being defined between the two electrodes 72, 74, and a distal (or tip) section 75 between the downstream electrode 74 and the exit end 56 of the capillary tube 60. A voltage applied between the two electrodes 72, 74 generates heat in the heated section 73 based on the resistivity of the stainless steel or other material making up the capillary tube 60 or heating system 70, and other parameters such as the cross-sectional area and length 66 of the heated section 73.

Figure 5:
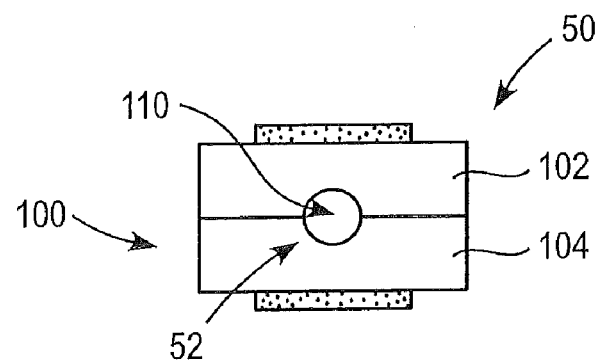
FIG. 5 is a side view of a capillary unit in the form of a laminar structure in accordance with another embodiment.

FIG. 5 shows a side view of a capillary unit 50 in the form of a laminate or laminar structure 100. In accordance with this embodiment, the capillary unit 50 is comprised of a laminar structure, wherein, several layers of material are bonded together to create the fluidic path or capillary passage 52. As shown in FIG. 5, the capillary unit 50 can be made from a laminate structure 100, wherein the fluidic or capillary passage 52 comprises a channel 110 in a first layer 102 and a second layer 104 overlying the first layer 102 encloses the channel 110 as described in commonly owned U.S. Pat. Nos. 6,701,921 and 6,804,458, which are incorporated herein in its entirety.

Figure 6:
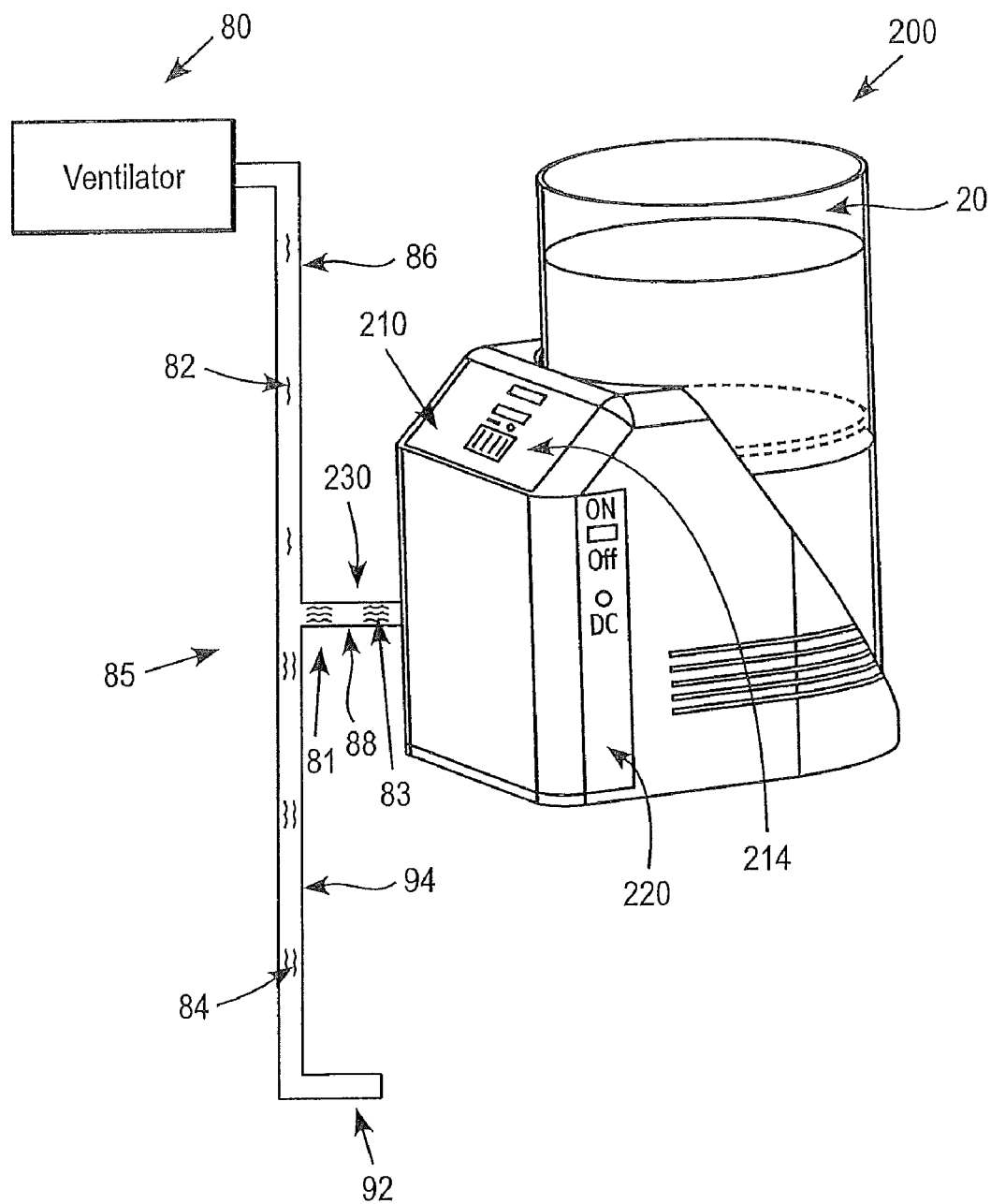
FIG. 6 is a perspective view of a humidification system in accordance with one embodiment.
Figure 7:
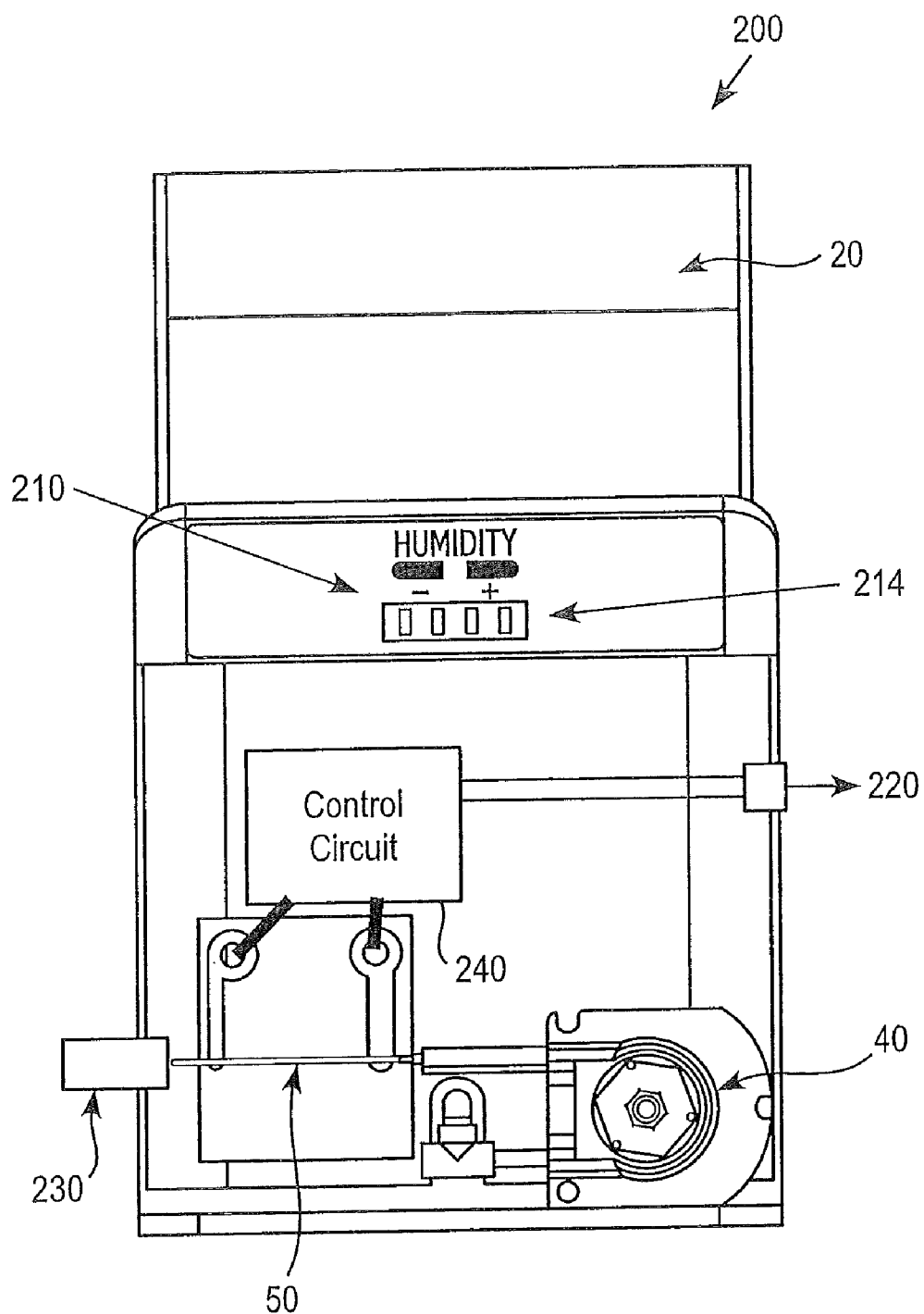
FIG. 7 is a side cross-sectional view of the humidification system as shown in FIG. 6 showing a control system.

As shown in FIGS. 6 and 7, the liquid supply 20, the filter assembly 30, the pumping unit 40 and the capillary unit 50 are preferably self-contained within a base unit 200. The base unit 200 also includes a humidity control system 210, a power source 220 preferably in the form of a low voltage DC source (a direct current or continuous current source), such as a wall transformer, an outlet 230 to the ventilator circuit 85, and an electronic control circuit 240. The humidity control system 210 includes a humidity detector or sensor (not shown) and a humidity display 214 located on an exterior surface of the base unit 200. The humidity control system 210 is configured such the speed of the pumping unit 40 can be altered or changed to provide the humidified gas stream 84 with the desired relative humidity (RH).

The electronic control system 240 controls the speed of the pumping unit 40 and power to the electrodes attached to the capillary unit 50. In accordance with one embodiment, an algorithm to control power can be based on monitoring resistance or temperature of the capillary unit 50. It can be appreciated that by changing the speed of the pumping unit 40, which alters or changes the liquid material's 24 (i.e., water) flow rate, a shift in the relative humidity (RH) of the humidified air stream 84 can be achieved within milliseconds. In addition, by measuring patient airflow (or other demand for humidified air), the relative humidity within the system 10 can be controlled, such that the relative humidity can remain constant by responsively changing the flow rate of the water 24 to the capillary unit 50. Accordingly, the rate of humidification may be varied almost instantaneously in response to changes in flow rate of air from the ventilator.

The base unit 200 also includes an outlet 230 from the capillary unit 50 to the ventilator circuit 85 comprised of a ventilator supply tube 86 and an aerosol supply tube 88. The ventilator supply tube 86 and the aerosol supply tube 88 preferably have a connection wherein the aerosol stream 83 from the capillary unit 50 is entrained in the air stream 82 from the ventilator 80. It can be appreciated that any aerosols 81 associated with the aerosol stream 83 evaporate in the air stream 82 when the air stream 82 and the aerosol stream 83 are combined to form the humidified gas stream 84.

Figure 8:
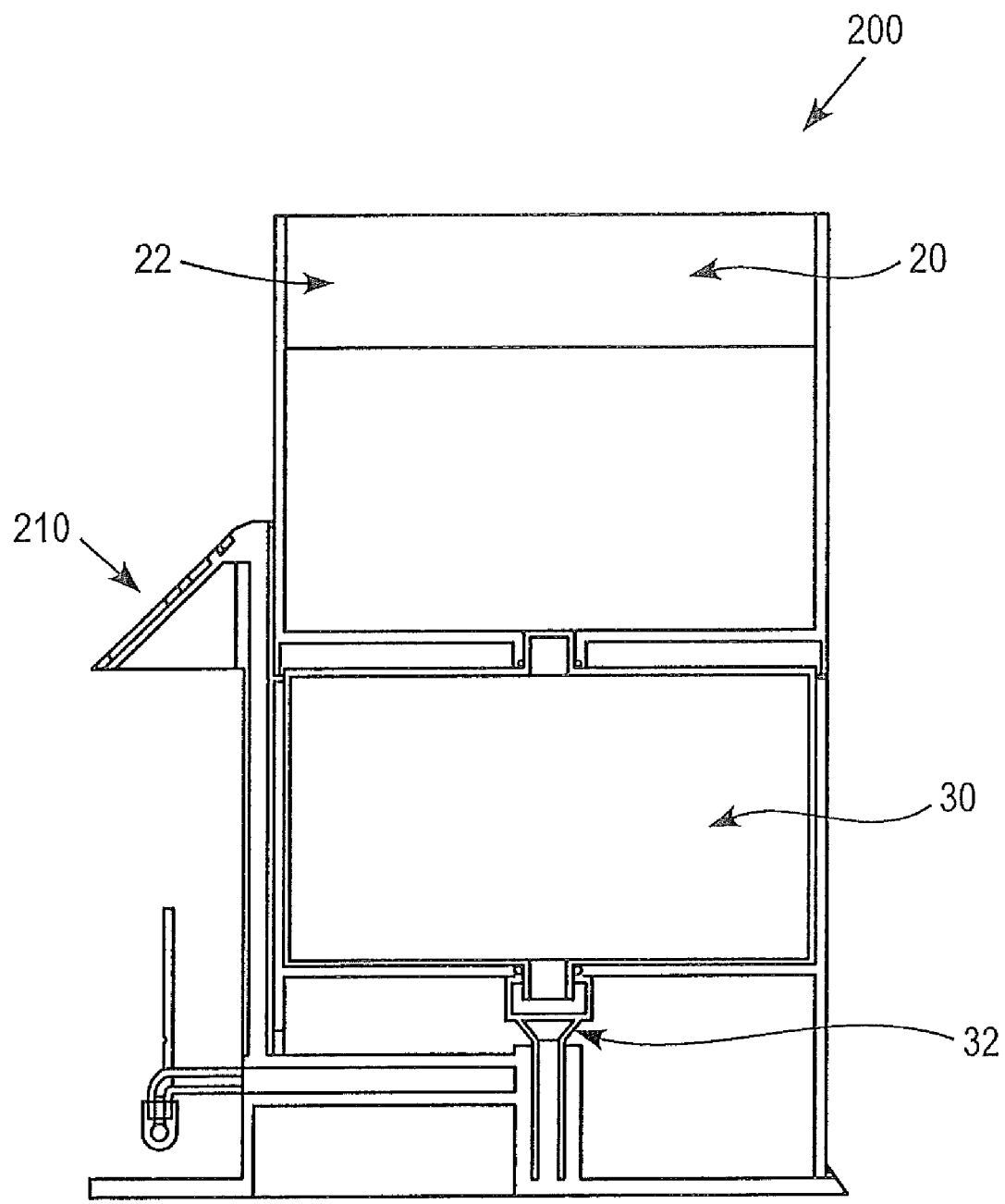
FIG. 8 is a side cross-sectional view of the humidification system as shown in FIG. 6 showing a pressurized water supply.

The filter assembly 30 as shown in FIG. 8 is preferably connected to the pumping unit 40 with a check valve 32, which allows for the removal of the liquid supply 20 from the base unit 200. In use, the reservoir 22 containing a liquid supply 20 is preferably a replaceable unit, wherein a new source of water or other suitable water 24 can be supplied as needed.

FIGS. 9-11 show relationships for power, water flow rate and pressure for three capillary geometries. As shown in FIG. 9, the table shows the flow rate versus power for a capillary unit 50 comprised of a K32EG inner diameter capillary passage 52 having an inner diameter of about 0.0073 inches and a length of about 1.3 inches. FIGS. 10 and 11 show the same relationships for a capillary unit 50 having an inner diameter of about 0.0048 inches (32 Gauge) and a length of about 1.3 inches, and a capillary unit 50 having an inner diameter of about 0.0073 inches (K32EG), a length of about 1.3 inches and an orifice of about 0.00314 inches, respectively.

FIG. 12 shows the relative humidity produced by the system 10 as illustrated in FIG. 1 using a capillary unit 50 having an inner diameter of about 0.0073 inches and a length of about 1.3 inches. The measurements of relative humidity (RH) were taken at the end of a three foot respiratory tube, which would correspond with approximately the location where the patient would interface with the system 10.

FIG. 13 is a table showing the particle size of an aerosol exiting a capillary passage (measured 1 inch from the capillary) versus power. As shown in FIG. 13 as the amount of power supplied to the capillary increases due to the temperature increase the particle size of the aerosol decreases.

In accordance with another embodiment, it can be appreciated that microbial activity can be rendered harmless. For example, a capillary passage 52 having an inner diameter of about 0.008 inches being fed 1.65 cc/minute of water, which is heated to approximately 150 degrees Celsius can provide aerosolized water, which has been rendered without microbial activity.

While various embodiments have been described, it is to be understood that variations and modifications may be resorted to as will be apparent to those skilled in the art. Such variations and modifications are to be considered within the purview and scope of the claims appended hereto.

What is claimed is:

1. A respiratory humidification system, comprising:
   a capillary passage in communication with a ventilator, the ventilator adapted to deliver an air stream;
   a heater operable to at least partially vaporize water in the capillary passage;
   a pumping unit adapted to supply water to the capillary passage, wherein the water upon heating is at least partially vaporized to form an aerosol stream, and wherein the aerosol stream is combined with the air stream to form a humidified air stream;

a controller having an on-off switch and programmed such that the controller is configured to continuously operate the pump and to maintain the capillary in a heated condition when the controller switch is on; and a water recirculation arrangement to accommodate continuous operation of the pumping unit.

2. The system of claim 1, wherein the pumping unit delivers the water to the capillary passage at a pressure of approximately 10 to 80 psig.

3. The system of claim 1, wherein the water is supplied from a pressurized water supply.

4. The system of claim 3, further comprising a filter adapted to demineralize water supplied from the pressurized water supply.

5. The system of claim 1, wherein the heater is adapted to produce aerosol particles having a particle size of less than 2 microns.

6. The system of claim 1, wherein the aerosol stream from the capillary passage is directed in a coaxial relation with respect to the air stream from the ventilator.

7. The system of claim 3, wherein the capillary passage is a capillary tube having at least one heater body operable to heat the capillary tube to a temperature range effective to at least partially vaporize the pressurized water in the capillary tube.

8. The system of claim 1, further comprising a flow tube having an inlet end in fluid communication with an outlet of the capillary passage and an outlet adapted for connection to a patient interface device.

9. The system of claim 1, wherein the capillary passage comprises:

a laminate body having the capillary passage therein, the capillary passage being located between opposed layers of the laminate body which are bonded together; and a heater arranged to heat the water in the capillary passage into at least a partially vaporized state.

10. The system of claim 1, wherein the aerosol stream includes aerosols having a particle size of less than 2 microns and wherein the aerosols evaporate upon entrainment with the air stream.

11. A respiratory humidification system, comprising:

a heated capillary passage adapted to receive water from a pressurized water supply, which is at least partially vaporized within the heated capillary passage to form an aerosol stream, the heated capillary passage comprising:

a capillary passage adapted to form an aerosol when the pressurized water in the capillary passage is heated to volatilize at least some of the pressurized water therein; and a heater arranged to heat the pressurized water in the capillary passage into at least a partially vaporized state;

a pumping unit adapted to supply the pressurized water to the capillary passage;

a filter operable to demineralize the pressurized water; and a ventilator adapted to deliver an air stream, and wherein the aerosol stream is combined with the air stream to form a humidified gas stream.

12. The system of claim 11, wherein the pumping unit delivers the pressurized water to the capillary passage at a pressure of approximately 10 to 80 psig.

13. The system of claim 11, wherein the capillary passage is contained within a housing that interfaces with the air stream from the ventilator.

14. The system of claim 11, wherein the aerosol stream from the capillary passage is directed coaxially with the air stream from the ventilator.

15. The system of claim 11, further comprising a flow tube having an inlet end in fluid communication with an outlet of the capillary passage and an outlet adapted for connection to a patient interface device.

16. The system of claim 11, wherein the capillary passage is comprised a laminate body having the capillary passage therein, the capillary passage being located between opposed layers of the laminate body which are bonded together.

17. A respiratory humidification system having an enhanced capacity to operate with mineral laden water, the system comprising:

a coated capillary passage whose operating temperature is in the range of 120 to 130 degrees Celsius, and which is in communication with a ventilator, the ventilator adapted to deliver an air stream;

a heater operable to at least partially vaporize water in the capillary passage; and a pumping unit adapted to supply water to the capillary passage, wherein the water upon heating is at least partially vaporized to form an aerosol stream, and wherein the aerosol stream is combined with the air stream to form a humidified air stream further comprising:

a controller having an on-off switch and programmed such that the controller is configured to continuously operate the pump and to maintain the capillary in a heated condition when the controller switch is on; and a water recirculation arrangement to accommodate continuous operation of the pumping unit.

* * * * *